United States Patent [19]
Short et al.

[11] Patent Number: 5,161,535
[45] Date of Patent: Nov. 10, 1992

[54] MEDICAL ULTRASOUND IMAGING SYSTEM HAVING A PARTITIONED MENU

[75] Inventors: Kerry C. Short, Bradford; Albert F. Koch, III, Newburyport, both of Mass.

[73] Assignee: Hewlett-Packard Company, Palo Alto, Calif.

[21] Appl. No.: 720,149

[22] Filed: Jun. 24, 1991

[51] Int. Cl.$^5$ .............................................. A61B 8/00
[52] U.S. Cl. ......................... 128/660.01; 364/413.13; 340/712
[58] Field of Search .................. 128/660.01; 340/700, 340/711, 712; 364/200, 900

[56] References Cited

U.S. PATENT DOCUMENTS

| | | | |
|---|---|---|---|
| 4,608,662 | 8/1986 | Watanabe et al. | 364/900 |
| 4,644,486 | 2/1987 | Cannon et al. | 364/570 |
| 4,821,030 | 4/1989 | Batson et al. | 340/712 |
| 4,870,561 | 9/1989 | Love et al. | 364/200 |
| 4,922,909 | 5/1990 | Little et al. | 364/413.13 |
| 5,056,059 | 10/1991 | Tivig et al. | 340/712 |

OTHER PUBLICATIONS

Toshiba SSH-140A advertisement.
Ultramark 9 advertisement.
GE Radius Ultrasound System advertisement.

Primary Examiner—Francis Jaworski
Assistant Examiner—George Manuel

[57] ABSTRACT

An ultrasound imaging system and method for controlling the system has a control panel which includes menu items divided into system mode menu items for selecting a system mode, and control set menu items for selecting functions corresponding to a selected system mode menu item. The system mode menu items are always available for selection independent of which control set is being displayed. An electro-luminescent touch panel displays the menu items and the user selects a menu item by touching the item on the panel. Rotatable controls are located on the control panel adjacent to the display and displayed menu items which define the functions of the controls. More then one system mode may be activated at the same time by selecting each desired system mode in sequence from the system mode menu items. The system modes include 2D, M mode, Color flow, and Doppler imaging. A second panel displays non-imaging related functions.

20 Claims, 16 Drawing Sheets

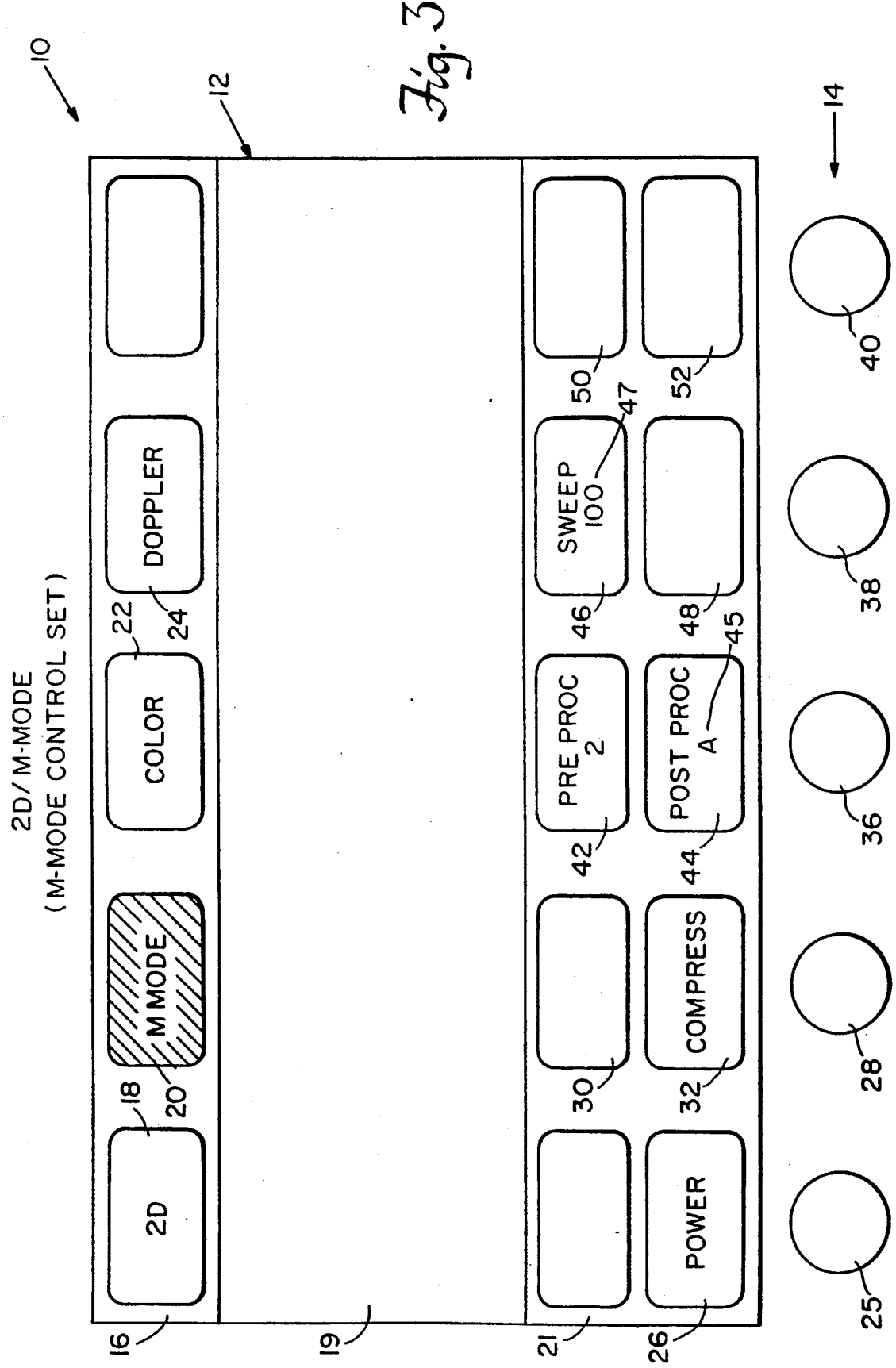

ULTRASOUND SYSTEM STATES

System Inputs

| CURRENT STATE | 2D | MMODE | COLOR | DOPPLER |
|---|---|---|---|---|
| 2D | 2D | 2D/MM | 2D/CF | 2D*/PWA |
| 2D* | 2D | 2D/MM | 2D*/CF | 2D*/PWA |
| 2D/MM | 2D | 2D | 2D/CF/MM | 2D/PWA |
| 2D/CF | 2D | 2D/CF/MM | 2D | 2D/CF/PWx |
| 2D*/CF | 2D | 2D/CF/MM | 2D* | 2D*/CF/PWA |
| 2D/PWA | 2D | 2D/MM | 2D/CF/PWx | 2D |
| 2D*/PWA | 2D | 2D/MM | 2D/CF/PWx | 2D |
| 2D/PWS | 2D | 2D/MM | 2D*/CF/PWS | 2D |
| 2D*/PWS | 2D | 2D/MM | 2D*/CF/PWS | 2D |
| 2D*/CWS | 2D | 2D/MM | 2D/CF/CWS | 2D |
| 2D/CWx | 2D | 2D/MM | 2D/CF/CWx | 2D |
| CWS | --- | --- | --- | --- |
| 2D/CF/MM | 2D | 2D/CF | 2D/MM | 2D/CF/PWx |
| 2D*/CF/PWA | 2D | 2D/CF/MM | 2D*/PWA | 2D/CF |
| 2D*/CF/PWS | 2D | 2D/CF/MM | 2D*/PWS | 2D/CF |
| 2D/CF/PWx | 2D | 2D/CF/MM | 2D*/PWA | 2D/CF |
| 2D*/CF/CWS | 2D | 2D/CF/MM | 2D*/CWS | 2D/CF |
| 2D/CF/CWx | 2D | 2D/CF/MM | 2D/CWx | 2D/CF |

\* = Frozen or Triggered 2D Image
CWx/PWx = Doppler Search States
--- = Control Not Available

Fig. 6

ULTRASOUND
SYSTEM STATES

System Inputs

| CURRENT STATE | PW | CW | SPECTRAL | TRIGGER |
|---|---|---|---|---|
| 2D | --- | --- | --- | 2D* |
| 2D* | --- | --- | --- | 2D |
| 2D/MM | --- | --- | --- | --- |
| 2D/CF | --- | --- | --- | 2D*/CF |
| 2D*/CF | --- | --- | --- | 2D/CF |
| 2D/PWA | 2D | 2D*/CWS | 2D*/PWS | 2D*/PWA |
| 2D*/PWA | 2D | 2D*/CWS | 2D*/PWS | 2D/PWA |
| 2D/PWS | 2D | 2D*/CWS | 2D/PWA | 2D*/PWS |
| 2D*/PWS | 2D | 2D*/CWS | 2D*/PWA | 2D/PWS |
| 2D*/CWS | 2D*/PWS | 2D | 2D/CWx | --- |
| 2D/CWx | 2D/PWA | 2D | 2D*/CWS | --- |
| CWS | --- | --- | --- | --- |
| 2D/CF/MM | --- | --- | --- | --- |
| 2D*/CF/PWA | 2D/CF | 2D/CF/CWS | 2D*/CF/PWS | --- |
| 2D*/CF/PWS | 2D/CF | 2D*/CF/CWS | 2D/CF/PWx | --- |
| 2D/CF/PWx | 2D/CF | 2D/CF/CWx | 2D*/CF/PWS | 2D*/CF/PWA |
| 2D*/CF/CWS | 2D*/CF/PWS | 2D/CF | 2D/CF/CWx | --- |
| 2D/CF/CWx | 2D/CF/PWx | 2D/CF | 2D*/CF/CWS | --- |

Fig. 6 CONT.

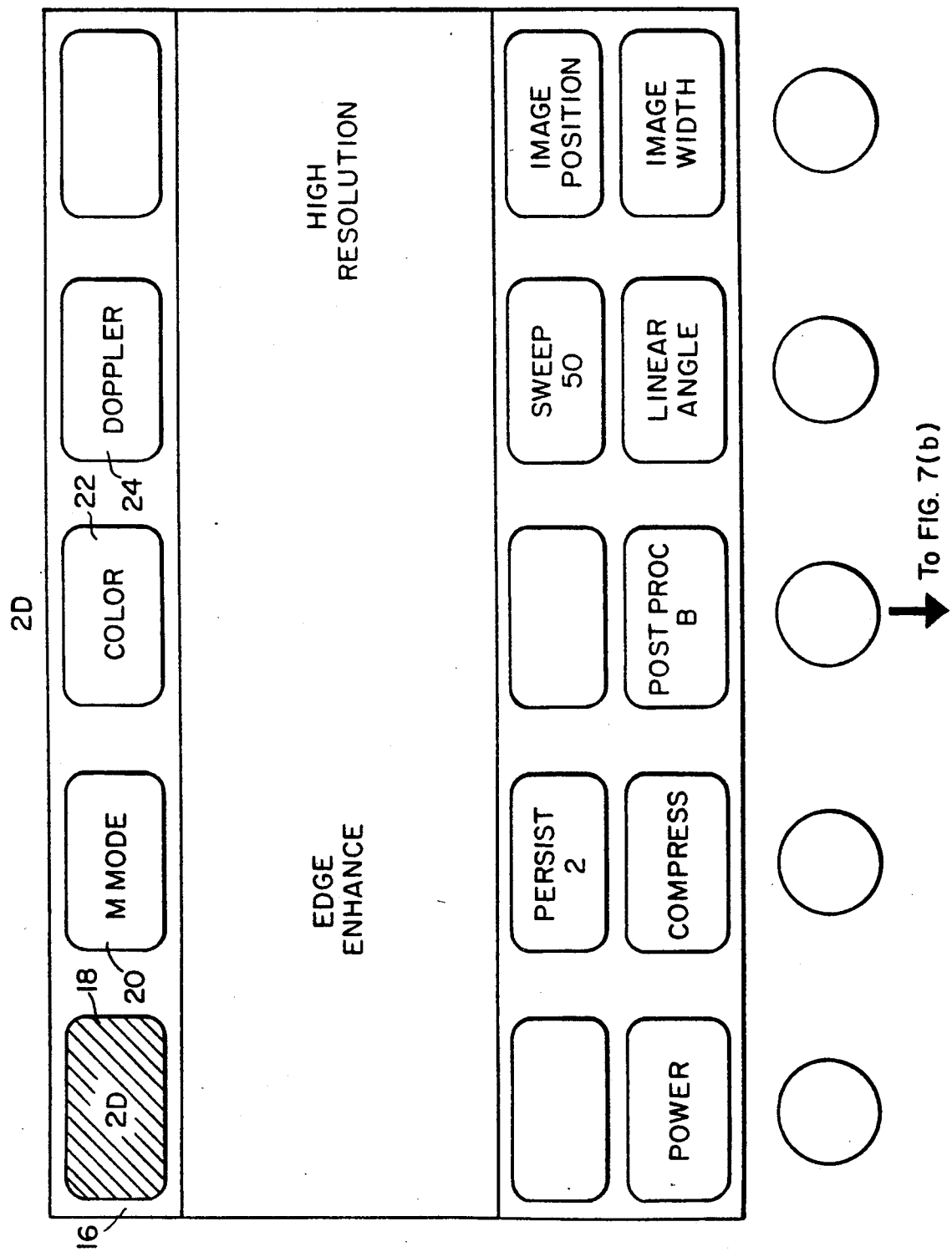

MEDICAL ULTRASOUND IMAGING SYSTEM HAVING A PARTITIONED MENU

BACKGROUND OF THE INVENTION

Medical ultrasound imaging systems have evolved into complex instruments offering a wide variety of imaging modalities including two dimensional imaging mode (2D) which may have a sector or linear format, M Mode (MM), Color Flow (COLOR), and Doppler (DOPPLER) imaging. Each modality requires a set of user controls unique to that modality. Not only is each mode operational independent of the other modes, but they may also be combined into a variety of composite modes. These composite modes include 2D/MM, 2D/COLOR, 2D/COLOR/MM, 2D/DOPPLER and 2D/COLOR/DOPPLER. The complexity of the user controls required to operate the system in a composite mode is increased substantially since the user controls for each mode making up the composite mode must be readily available to the user. The situation is further complicated since some controls must be dedicated to system functions which are independent of the selected modality, e.g., VCR and hard copy controls.

Medical ultrasound imaging systems are typically used to image patients in real time. Thus, the user must be able to operate the system controls efficiently. As the complexity and functionality of the ultrasound system increases, traditional hard-wired controls dedicated to each function produce more crowded control panels which are more difficult for the user to operate in real time. A control panel for an ultrasound system having a dedicated control for each available function would require over 100 controls.

Ultrasound system control panels have been developed which minimize the control set available to the user at any one time, dependent on the selected ultrasound mode, to reduce control complexity. One such minimum control set approach uses programmable "soft keys" whose functions change dependent upon the selected mode. A new function may be assigned to each soft key as the mode change and displayed on a display device.

Hierarchical menus, such as "pull-down" menus, have also been used to minimize the control set available to the user. Each menu is displayed on a display device and typically offers a list of available menu items related to a particular mode or function from which the user selects one item. This selection either produces the desired function or causes another lower level menu to be displayed which offers more menu items related to the first selected item. The selection process is repeated until the desired ultrasound system function is selected. The user may need to go through several menu layers to reach the desired function. From there the user may need to back track through several menu layers to reach another desired function.

SUMMARY OF THE INVENTION

The present invention provides a control panel for a medical ultrasound imaging system which offers the user the control simplicity of a reduced set of control functions for each ultrasound mode (control set) while allowing the user instant access to any control set regardless of the current system mode.

In general, in one aspect, the invention features an ultrasound imaging system having a control panel which includes menu items divided into system mode menu items for selecting a system mode, and control set menu items for selecting functions corresponding to a selected system mode menu item. Menu items are displayed on a control panel display so that the control set menu items displayed correspond to the selected system mode. The system mode menu items are always available for selection independent of which control set is being displayed.

Preferred embodiments include an electro-luminescent panel for displaying menu items. The electroluminescent panel may be a touch panel and the user selects a menu item by touching the item on the panel. Other embodiments include controls located on the control panel adjacent to the display and displayed menu items which define the functions of the controls. The controls include rotatable control knobs. More than one menu item may define functions available for a control, and one of the menu items is selected to define the current function of the control.

Other preferred embodiments include more then one system mode being activated at the same time by selecting each desired system mode in sequence from the system mode menu items. Control set menu items are displayed which correspond to the last selected system mode. The system modes include 2D, M mode, Color flow, and Doppler imaging.

Yet other preferred embodiments include another display for displaying menu items for controlling non-imaging functions.

In general, in another aspect, the invention features a method for controlling an ultrasound system including displaying system mode menu items on a display, selecting a system mode from the system mode menu items, and displaying the control set menu items of the selected system mode in addition to the system mode menu items.

Thus, the present invention has the advantages of offering the user of the system mode specific control sets without hiding the control sets under layers of menus, which would otherwise mask system functionality. Modes which may be activated simultaneously are easily activated from any current system mode, and the control set for each activated mode is easily accessible. The touch panel of this invention offers the user instant menu choice selection by touching the menu item itself, which enhances system controllability during real time medical ultrasound exams.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 3 is a plan view of the control panel of FIG. 2 displaying the M Mode menu.

FIG. 6 is a system state diagram for the ultrasound system of FIG. 1.

FIG. 7(a) through FIG. 7(e) are plan views of the control panel of FIG. 2 displaying menu changes in response to ultrasound system mode selections.

DESCRIPTION OF THE PREFERRED EMBODIMENTS

Figure 1:
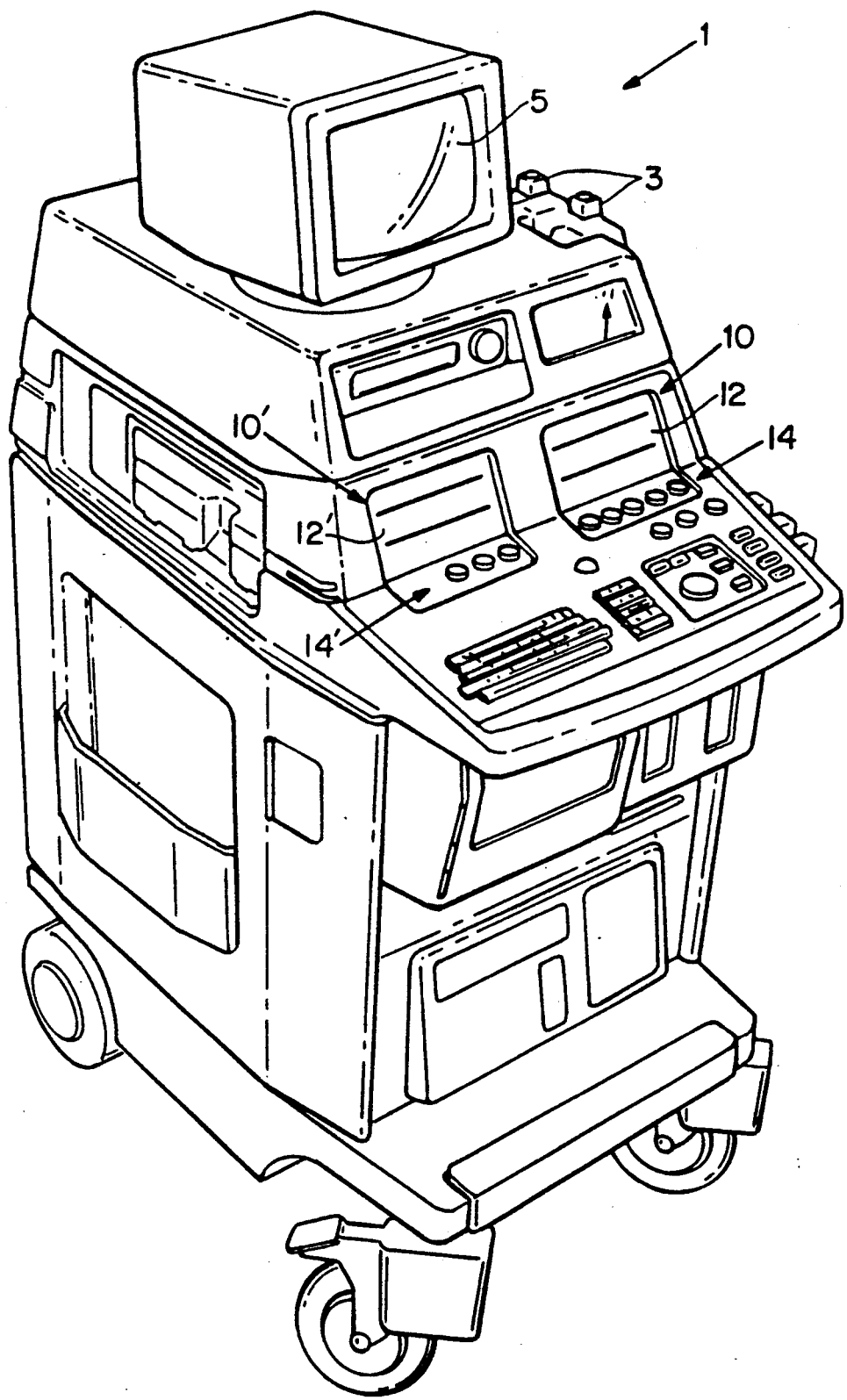
FIG. 1 is a perspective view of the medical ultrasound imaging system featuring the partitioned menu control panel of this invention.

Referring to FIG. 1, there is shown a medical ultrasound imaging system 1 having an ultrasonic imaging probe 3 for imaging a patient, and a display 5 for displaying the ultrasound image generated by the system. Two menu driven control panels 10 and 10' provide an improved user interface to the ultrasound system according to the invention.

Figure 2:
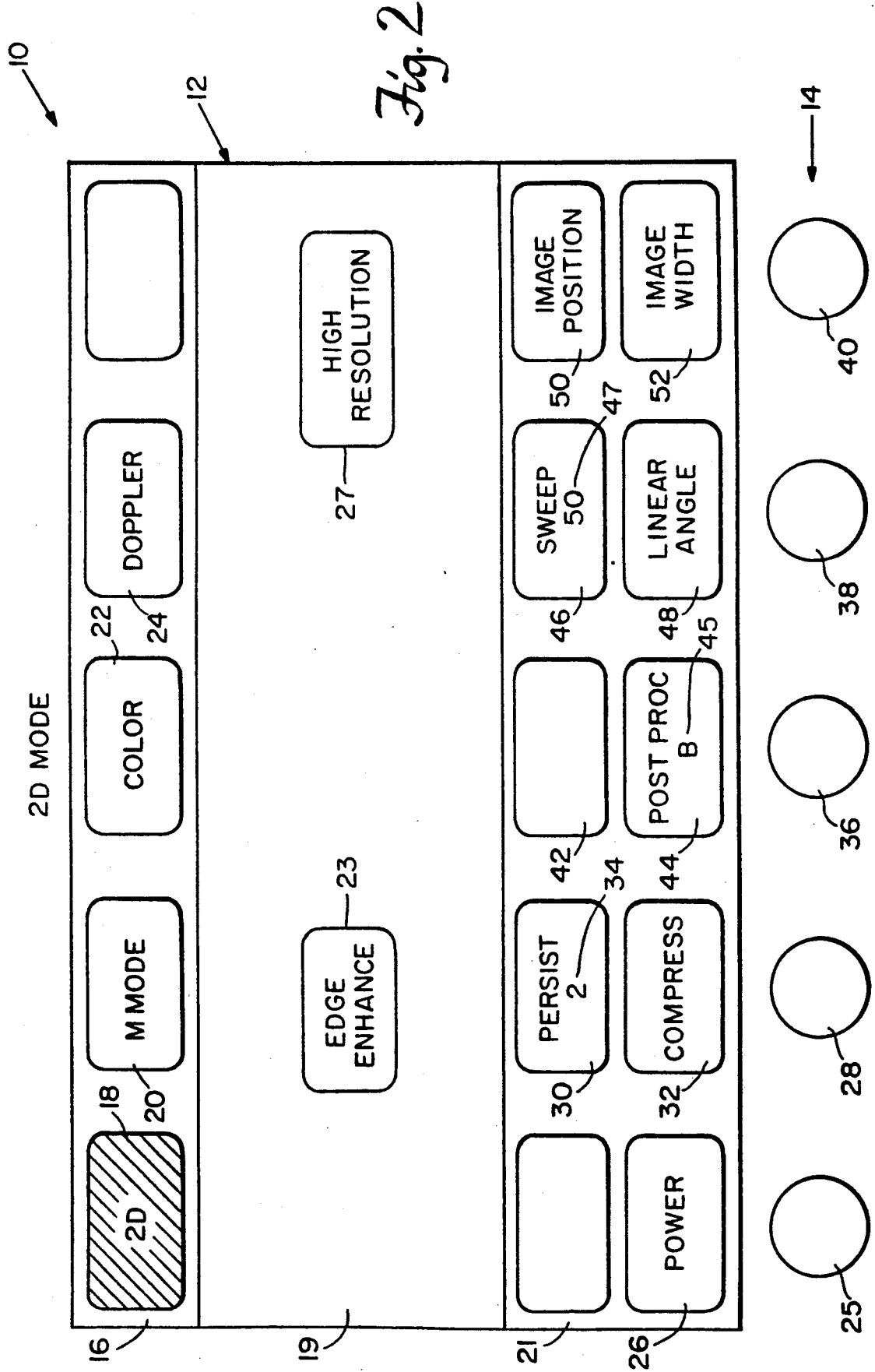
FIG. 2 is a plan view of the control panel of this invention displaying the 2D mode menu.

Referring to FIG. 2, the menu driven control panel 10 of the ultrasound imaging system 1 of FIG. 1 features a flat menu hierarchy to partition the ultrasound system controls into smaller control sets specific to each of the different system modes. The control sets are divided into menu items, with each menu item typically controlling one system function. Control panel 10 includes a flat electroluminescent touch panel 12 (EL panel) and soft controls 14 (FIG. 1) for displaying menu items to the user. The user touches a menu item displayed on the EL panel to select that menu item, and the ultrasound system responds accordingly. A row of soft controls 14, which are rotatable soft controls in the preferred embodiments described herein, is positioned below and adjacent to the EL panel. Each rotatable control operates according to a corresponding function displayed on the adjacent EL panel.

The minimum control set menu displayed on the EL panel 12 is divided into three groups of controls: a control set selection group 16 located at the top of the EL panel, a functional control group 19 located at the center of the EL panel, and a rotatable control group 21 located at the bottom of the EL panel adjacent to the row of rotatable controls 14.

The control set selection group 16 contains the control set entry points for each of the individual valid ultrasound modes, and remains available to the user regardless of the current operating mode of the system. Control set selection group 16 allows the user to select the 2D control set from menu item 18, the M-Mode control set from menu item 20, the COLOR control set from menu item 22, or the DOPPLER control set from menu item 24. If, for instance, a linear transducer is connected to the system and is active, M Mode is an invalid mode and therefore, menu item 20 will be empty.

When the user selects a control set by touching the appropriate control set selection menu item, the menu item is highlighted, and the remainder of the EL panel below the control set selection group 16 is reformatted to display the selected control set. The selected control set may display as menu items only valid functions for the selected system mode. Here, for instance, the 2D control group has been selected and menu item 18 is highlighted (shown as cross-hatching) indicating that the other groups of the EL panel display the 2D control set. When the user activates more than one system mode simultaneously, e.g., in a composite mode, only the last selected control group is displayed and the activated system modes are indicated in the appropriate control set menu item. Composite modes are discussed in detail below.

Functional control group 19 displays menu items offering the user various functions available in the selected control set. Here, the 2D control set offers the user an on/off EDGE ENHANCE function, menu item 23, and an on/off HIGH RESOLUTION function, menu item 27. Again, the desired function is activated by touching the corresponding menu item.

Rotatable control group 21 displays menu items indicating the function assigned or assignable to each of the rotatable controls 14 for the selected control set. The rotatable controls shown in FIG. 2, and discussed below, are for the 2D control set.

Rotatable control 25 controls the ultrasound system transmit power as indicated by the POWER menu item 26 adjacent to the control.

Rotatable control 28 has dual functionality and controls either image persistence as indicated by the PERSIST menu item 30 or image compression as indicated by the COMPRESS menu item 32. The user selects the function of control 28 by touching either PERSIST or COMPRESS. The selected menu item is highlighted. Further, the menu item associated with a rotatable control may also display the state of the control relating to that menu item, e.g., PERSIST menu item 30 also shows that rotatable control 28 has previously selected persistence mode 2 indicated by numeral 34.

Rotatable control 36 controls the 2D image post processing as indicated by the POST PROC menu item 44 adjacent to the control. Here, letter 45 indicates the current post processing selection, e.g., post processing map B.

Rotatable control 38 also has dual functionality and controls either the physiological trace (e.g., an ECG trace displayed along with the ultrasound image) sweep rate as indicated by the SWEEP menu item 46 or linear angle as indicated by the LINEAR ANGLE menu item 48. The SWEEP menu item is only displayed when the physiological measurement devices are configured to be operational, and the LINEAR ANGLE menu item is only displayed when a linear imaging transducer is active. The user selects the function of control 38 by touching either SWEEP or LINEAR ANGLE, and the selected menu item is highlighted. The SWEEP menu item also displays the current physiological trace sweep rate indicated by numeral 47, e.g., here indicating 50 mm/sec.

Rotatable control 40 also has dual functionality and controls either the image position as indicated by the IMAGE POSITION menu item 50 or image width as indicated by the IMAGE WIDTH menu item 52. The IMAGE POSITION menu item is only displayed when the 2D image is reduced in size.

Referring to FIG. 3, EL panel 12 displays the M mode control set activated by selecting the M MODE menu item 20 of the control set selection group 16. The M MODE menu item 20 is illuminated (shown by crosshatching) to indicate that the EL panel menu is displaying the M mode control set.

The M mode control set has fewer menu items than the 2D control set of FIG. 2. For instance, functional control group 19 contains no menu items. Rotatable control 25 retains it control over the ultrasound system transmit power as indicated by POWER menu item 26. Rotatable control 28 retains control over image compression as indicated by COMPRESS menu item 32, but no longer optionally controls persistence, i.e., menu item 30 is now empty. Rotatable control 36 now has dual functionality with M mode preprocessing now available on PRE PROC menu item 42 in addition to image postprocessing available on POST PROC menu item 44. Rotatable control 38 controls the M mode trace sweep rate (the physiological trace sweep rate is constrained to be the same as the M mode trace sweep rate in M mode) as indicated by SWEEP menu item 46, but no longer optionally controls the linear angle, i.e., menu item 48 is empty. Rotatable control 40 has no function in the M mode control set.

It should be noted that some controls may retain the last value assigned to them in a particular mode and restore those values when the mode is re-entered. For instance POST PROC is set to B in the 2D and A in the M mode, as indicated by letter 45 of the POST PROC menu item 44 of FIGS. 1 and 2, respectively. Similarly, the physiological trace sweep rate is set to 50 mm/sec in the 2D mode, and the M mode sweep rate is set to 100 mm/sec, as indicated by numeral 47 of SWEEP menu item 46 of FIGS. 1 and 2, respectively.

Figure 4A:
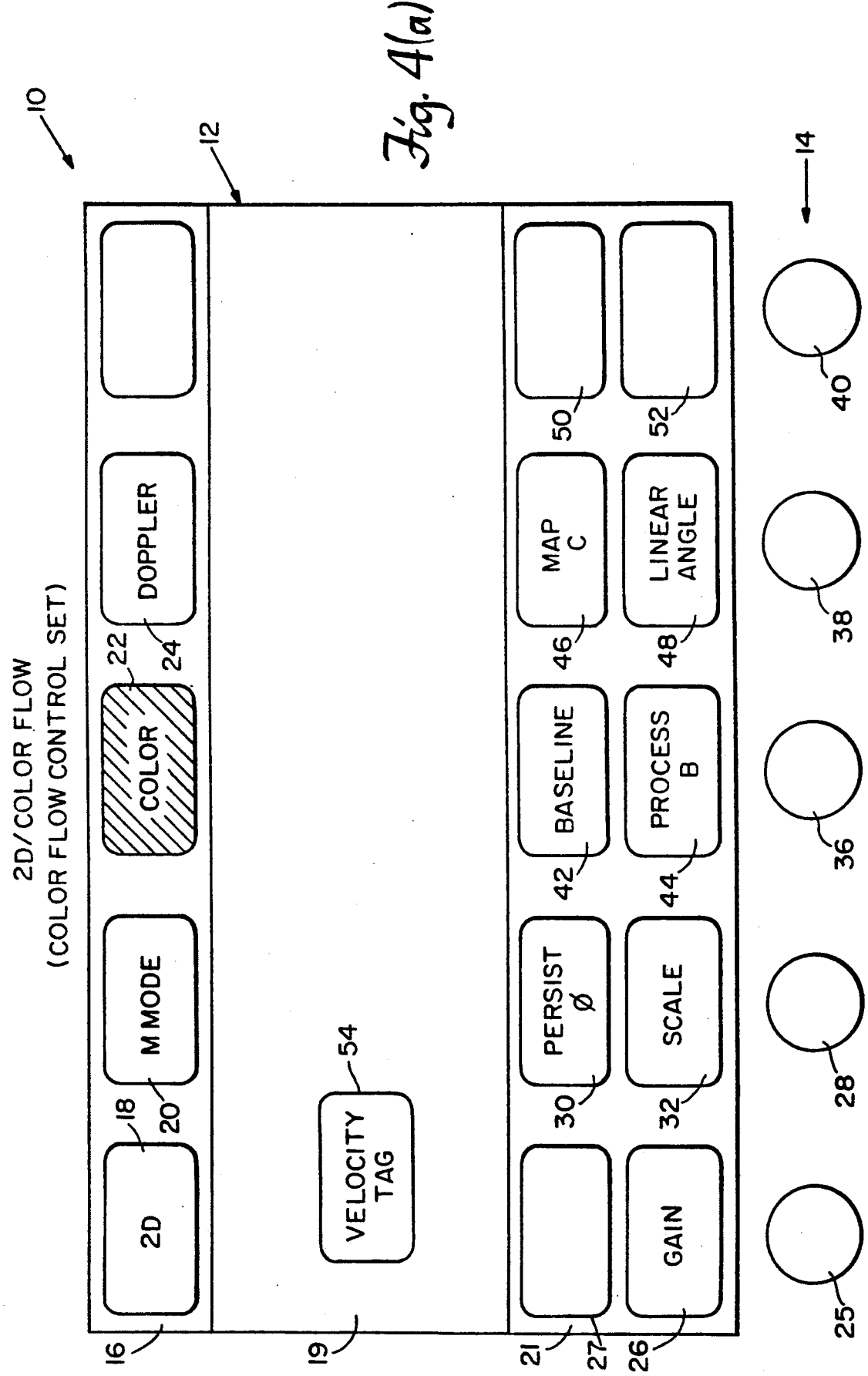
FIG. 4(a) and FIG. 4(b) are plan views of the control panel of FIG. 2 displaying Color Flow mode menus.

Referring to FIG. 4(a), EL panel 12 displays the color flow imaging mode control set activated by selecting the COLOR menu item 22 of the control set selection group 16. The COLOR menu item 22 is illuminated (shown by cross-hatching) to indicate that the EL panel menu is displaying the color flow imaging control set.

Functional control group 19 of the color flow imaging control set features a velocity tag function indicated by VELOCITY TAG menu item 54. The functions of the rotatable controls have also been redefined. Rotatable control 25 now controls color flow gain as indicated by GAIN menu item 26. Rotatable control 28 now optionally controls either color flow persistence as indicated by PERSIST menu item 30 or color scale as indicated by SCALE menu item 32. Rotatable control 36 now optionally controls color flow baseline as indicated by BASELINE menu item 42 or color flow process as indicated by PROCESS menu item 44. Rotatable control 38 now optionally controls either the color map selection as indicated by MAP menu item 46 or linear sector angle indicated by LINEAR ANGLE menu item 48. Again, the linear probe must be active to display LINEAR ANGLE menu item 48. Rotatable control 40 has no function in this control set.

Figure 4B:
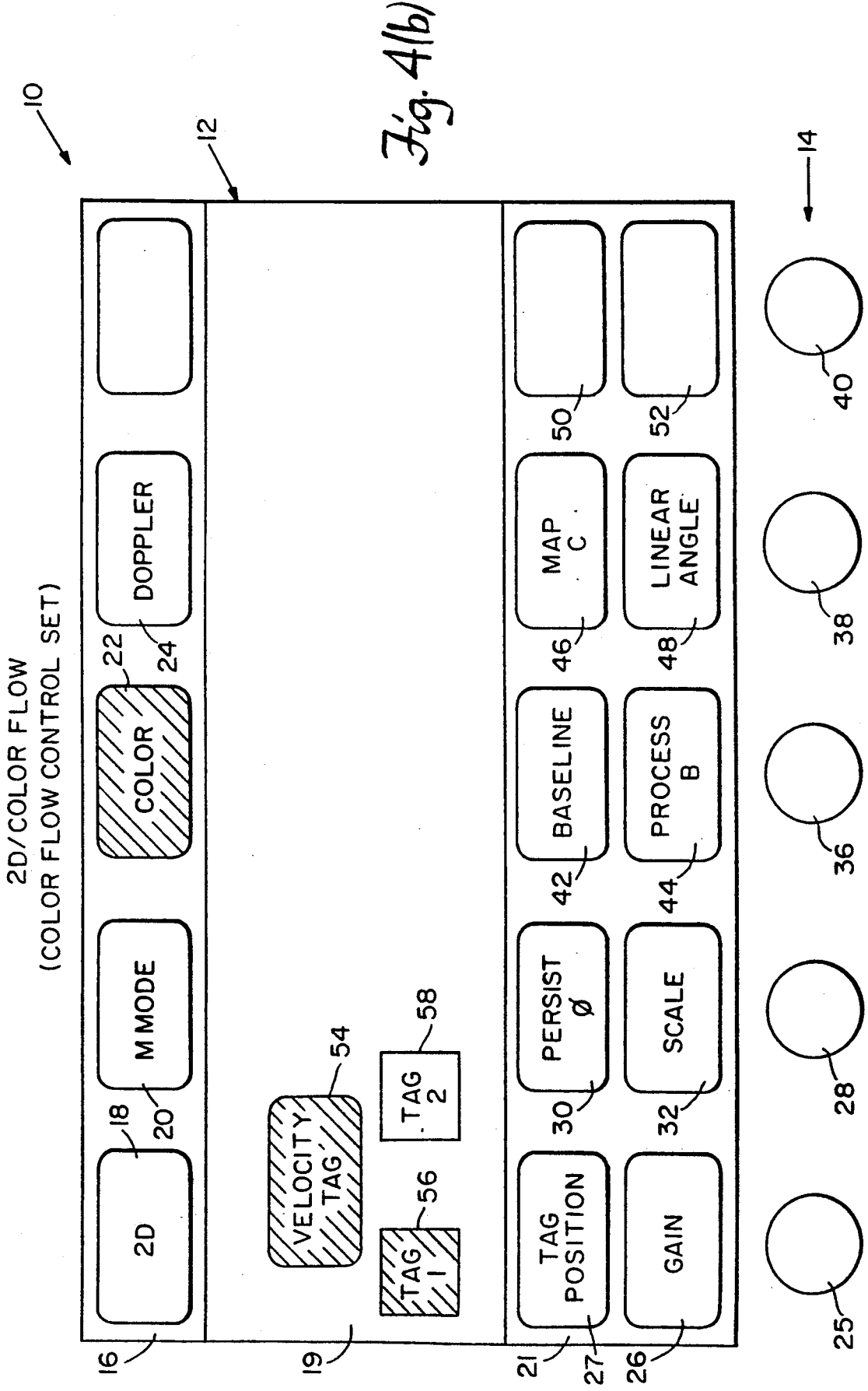

Referring to FIG. 4(b), the selection of VELOCITY TAG menu item 54 highlights the menu item (shown by cross-hatching) and causes the TAG 1 menu item 56 and TAG 2 menu item 58 to appear in the functional control group 19, and the TAG POSITION menu item 27 to appear over rotatable control 25. The TAG 1 and TAG 2 menu items operate in tandem such that exactly one of the TAG 1 or TAG 2 items is always selected. As shown here, velocity tag 1 is selected as indicated by the highlighted TAG 1 menu item 56. Rotatable control 25 now optionally controls the position of color tag 1 as indicated by the TAG POSITION menu item 27 or the color gain indicated by the GAIN menu item 26. Rotatable control 25 would optionally control the position of color tag 2 if the TAG 2 menu item 58 were selected.

Figure 5A:
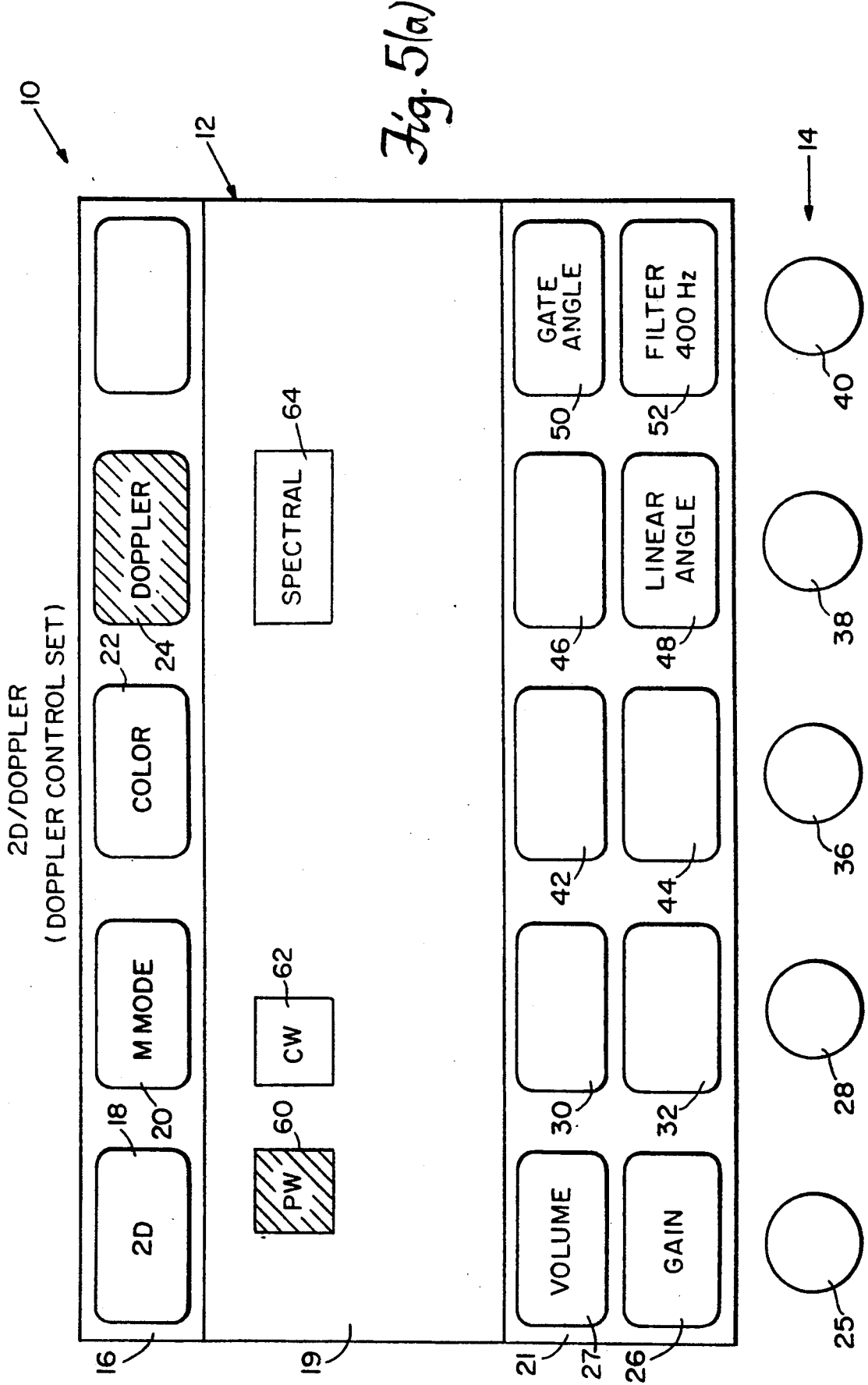
FIG. 5(a) and FIG. 5(b) are plan views of the control panel of FIG. 2 displaying Doppler mode menus.

Referring to FIG. 5(a), EL panel 12 displays the Doppler imaging mode control set activated by selecting the DOPPLER menu item 24 of the control set selection group 16. The DOPPLER menu item 24 is highlighted (shown by cross-hatching) to indicate that the EL panel menu is displaying the Doppler imaging mode control set.

Functional control group 19 of the Doppler imaging control set features a pulsed wave Doppler function indicated by the PW menu item 60, a continuous wave Doppler function indicated by the CW menu item 62, and a spectral display function indicated by the SPECTRAL menu item 64. The PW menu item 60 and the CW menu item 62 operate in tandem such that exactly one of the PW or CW menu item is selected at any one time, i.e., the user may select either the pulsed wave or the continuous wave Doppler mode, but not both. FIG. 5(a) shows PW as the selected mode as indicated by the highlighted PW menu item 60, and SPECTRAL menu item 64 as unselected.

Rotatable control 25 optionally controls either the Doppler audio volume as indicated by VOLUME menu item 27 or the Doppler gain as indicated by GAIN menu item 26. The VOLUME menu item is displayed when the Doppler audio signal has been activated by other system controls. Separate VOLUME and GAIN control values are retained by the system for the PW and CW modes. Rotatable control 38 again controls the linear angle as indicated by LINEAR ANGLE menu item 48, but is only displayed when a linear probe is connected to the system. Rotatable control 40 optionally controls the Doppler gate angle as indicated by the GATE ANGLE menu item 50 or the variable low frequency cutoff of the Doppler audio filter as indicated by the FILTER menu item 52. FILTER menu item 52 also displays the current filter setting, here shown as 400 Hz.

Figure 5B:
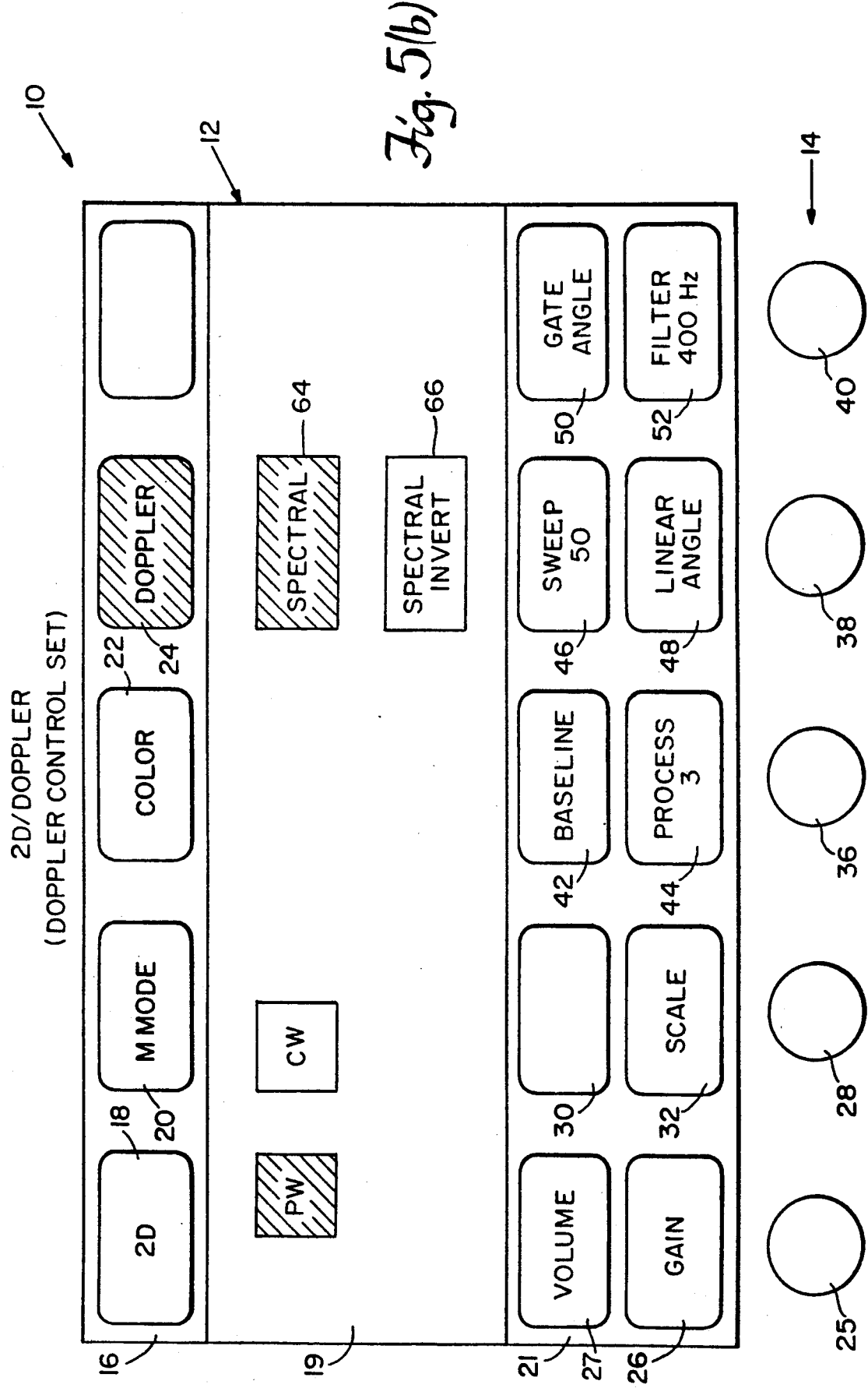

Referring to FIG. 5(b), the selection of the SPECTRAL menu item 64 highlights the menu item (shown by cross-hatching) and causes the SPECTRAL INVERT menu item 66 to appear in the functional control group 19. Selection of the SPECTRAL menu item also causes several new rotatable control menu items to appear. Rotatable control 28 now controls the scale of the displayed Doppler spectrum as indicated by the SCALE menu item 32. Rotatable control 36 now optionally controls either the baseline of the displayed Doppler spectrum as indicated by the BASELINE menu item 42 or the Doppler spectral processing as indicated by the PROCESS menu item 44. Rotatable control 38 now optionally controls either the spectral sweep rate as indicated by the SWEEP menu control 46, or the linear angle as indicated by the LINEAR ANGLE menu item 48.

Referring to FIG. 6 there is shown a table of ultrasound system states describing the various ultrasound system modalities available. The left hand column shows the current state of the system, the top row of the table shows the input to the system, i.e., the menu item selection made by the user, and the interior of the table show the system state that results from the system input. The system inputs listed as 2D, MMODE, COLOR, and DOPPLER correspond to the control set selection group 16 (FIG. 2) menu items 18, 20, 22, and 24, respectively. The PW, CW, and SPECTRAL system inputs correspond to the DOPPLER control set functional control group 19 (FIGS. 4(a) and 4(b)) menu items 60, 62, and 64, respectively, and are available as system inputs only when the DOPPLER control set has been activated. The TRIGGER system input is a hard-wired system control not displayed on the EL panel menu, and when activated causes the ultrasound image to be formed only upon the occurrence of some external event such as the R wave of an ECG trace. The image remains frozen during the period between triggers. Furthermore, the image is also frozen if the system is put into a Doppler search state, which allows the user to listen to high quality Doppler audio while positioning the Doppler gate in PW or the line cursor in CW.

As shown in the system state diagram, the system may always be returned to the nominal 2D imaging mode by selecting the 2D system input, i.e., the 2D menu item 18 (FIG. 2). When the system is in the 2D mode and the M MODE menu item 20 (FIG. 2) is selected, the system enters the 2D/M MODE(MM) state and the EL panel appears as shown in FIG. 3. When the system is in the 2D mode and COLOR menu item 22 is selected, the system enters the 2D/COLOR (CF) state and the EL panel appears as shown in FIG. 4(a). When the system is in the 2D mode and the DOPPLER menu item 24 is selected, the system enters the 2D(Triggered)/PW DOPPLER-AUDIO (PWA) state, and the EL panel appears as shown in FIG. 5(a). Once in the DOPPLER mode (PWA) the user may enter the PW search mode (PWx), the PW spectral mode (PWS), the CW search mode (CWx), or the CW spectral mode (CWS), by choosing the appropriate system inputs according to the state table.

The M MODE, COLOR and DOPPLER system inputs also operate to toggle the system out of the corresponding mode. For instance, if the system is in the 2D/MM state and the M MODE menu item 20 (FIG. 3) is selected, the system will return to the 2D state. Similarly, if the system is in the 2D/CF state and the COLOR menu item 22 (FIG. 4(a)) is selected, the system will return to the 2D state. If the system is in any 2D/PW or 2D/CW Doppler state and the DOPPLER menu item (FIG. 5(a)) is selected, the system will return to the 2D state.

When the system is in the 2D/MM state and COLOR menu item 22 (FIG. 3) is selected, the system enters the 2D/CF/MM composite mode state and the EL panel displays the color flow control set of FIG. 4(a). The EL panel would display the M mode control set of FIG. 3 if the system were first put into the 2D/CF state and then M MODE was selected to put the system in the 2D/CF/MM composite state. If the system is in the 2D/CF/MM state and DOPPLER is selected, the system enters the 2D/CF/PWx composite state and the EL panel appears as shown in FIG. 5(a). The PWx Doppler mode has replace the M Mode since simultaneous Doppler and M Mode are not allowed by the system.

An example of the EL panel menu response to changing system states is shown by FIGS. 6(a) through 6(e). The nominal 2D system state is reflected by the EL panel menu of FIG. 7(a) which shows the 2D control set of FIG. 2.

Figure 7B:
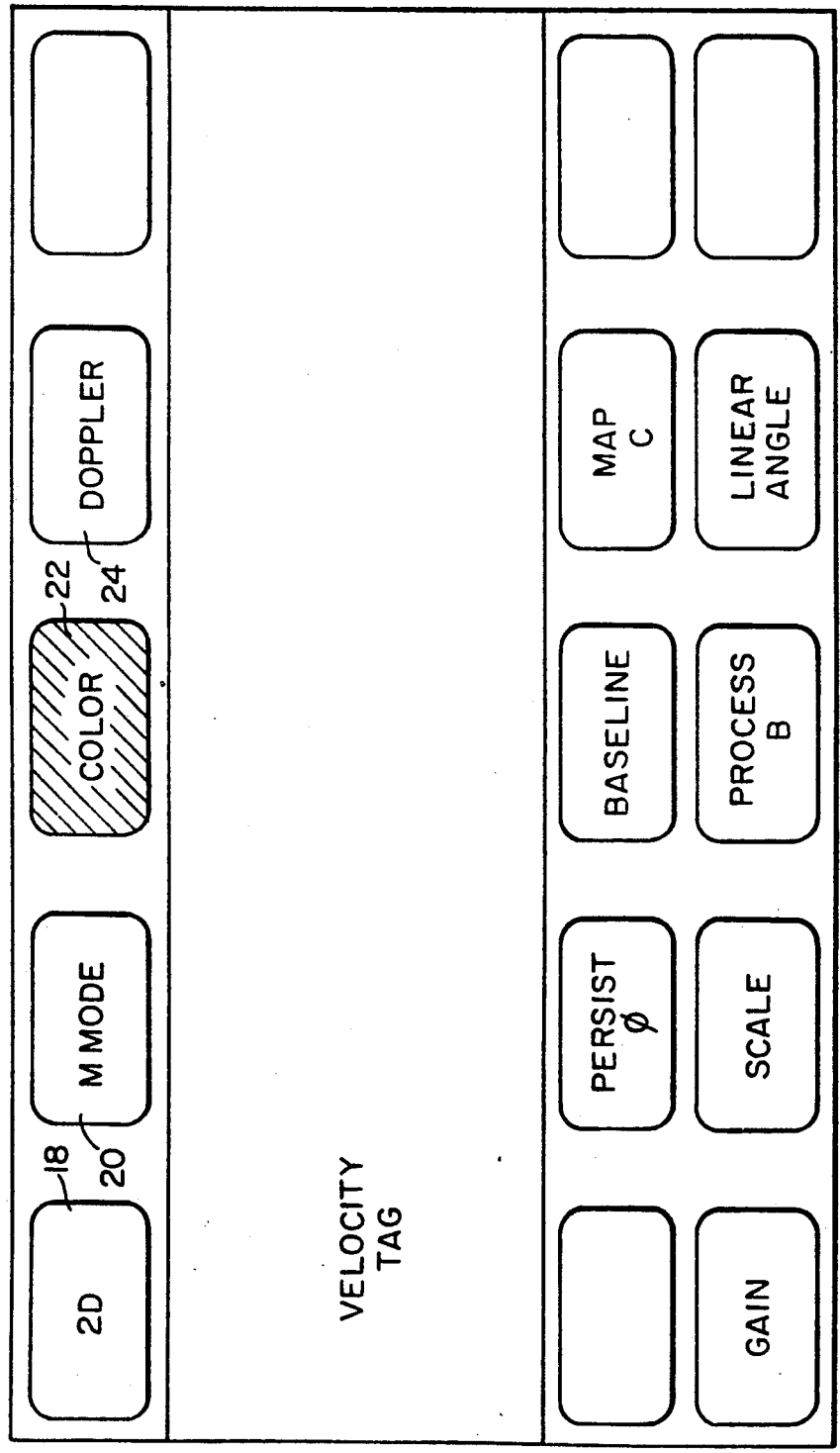

Upon selection of COLOR menu item 22 by the user, the system enters the 2D/CF mode and the EL panel menu transforms to that of FIG. 7(b) which shows the color flow control set of FIG. 4(a).

Figure 7C:
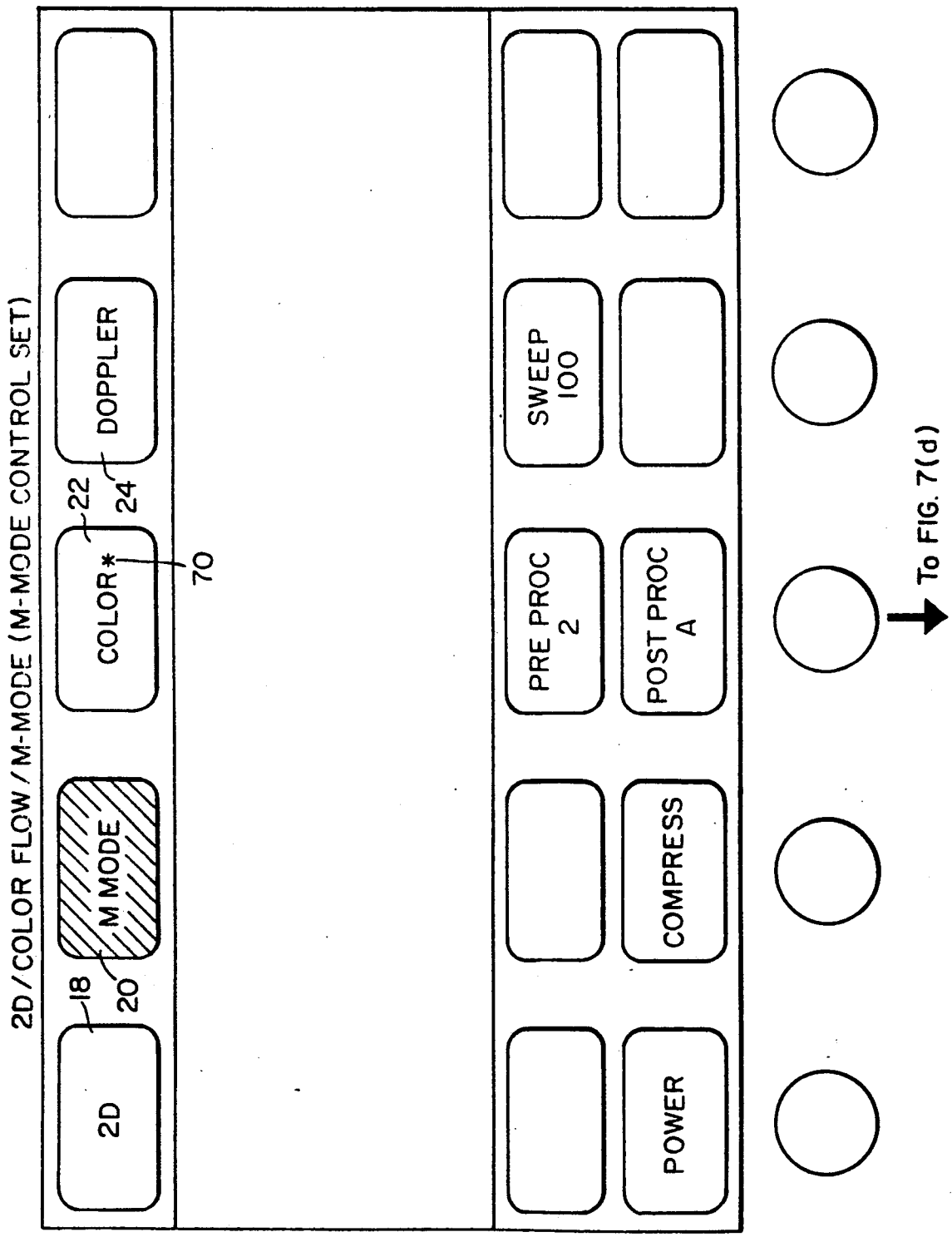

The user then selects M MODE menu item 20. The system enters the 2D/CF/MM composite mode and the EL panel responds as shown in FIG. 7(c) by displaying the M Mode control set of FIG. 3. An asterisk 70 is displayed in the COLOR menu item 22 to indicate that color flow mode is still active although the M mode control set is currently displayed. The color flow control set is available to the user, without changing the system state, by selecting the COLOR* menu item 22.

Figure 7D:
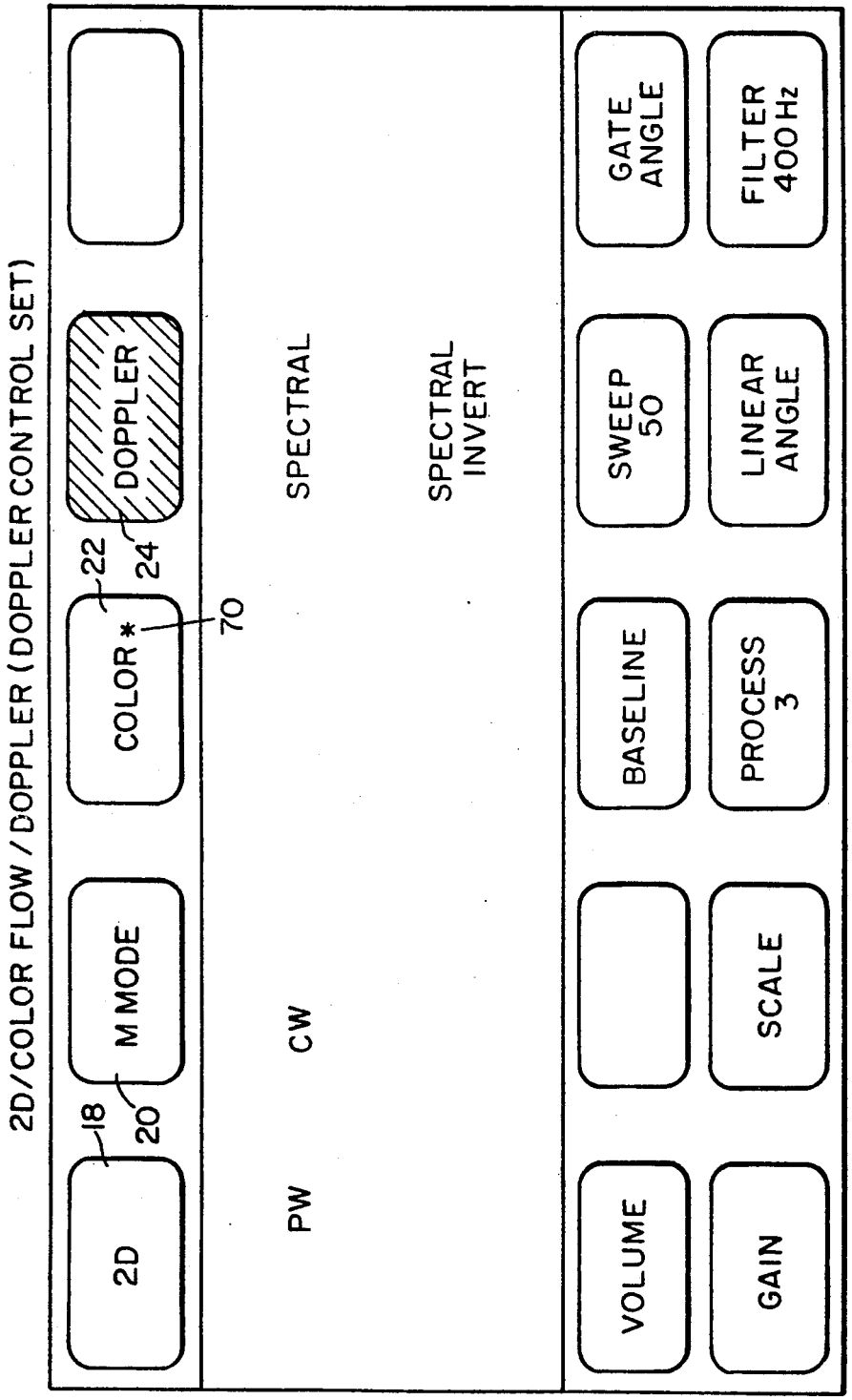

By selecting the DOPPLER menu item 24 the user then causes the system to enter the 2D/CF/Pwx composite color flow Doppler mode and the EL panel changes as shown in FIG. 7(d) to display the Doppler control set of FIG. 5(a). As discussed above, the Doppler mode has replaced M Mode. The color flow mode remains active as indicated by the asterisk 70 displayed in the COLOR menu item 22.

Figure 7E:
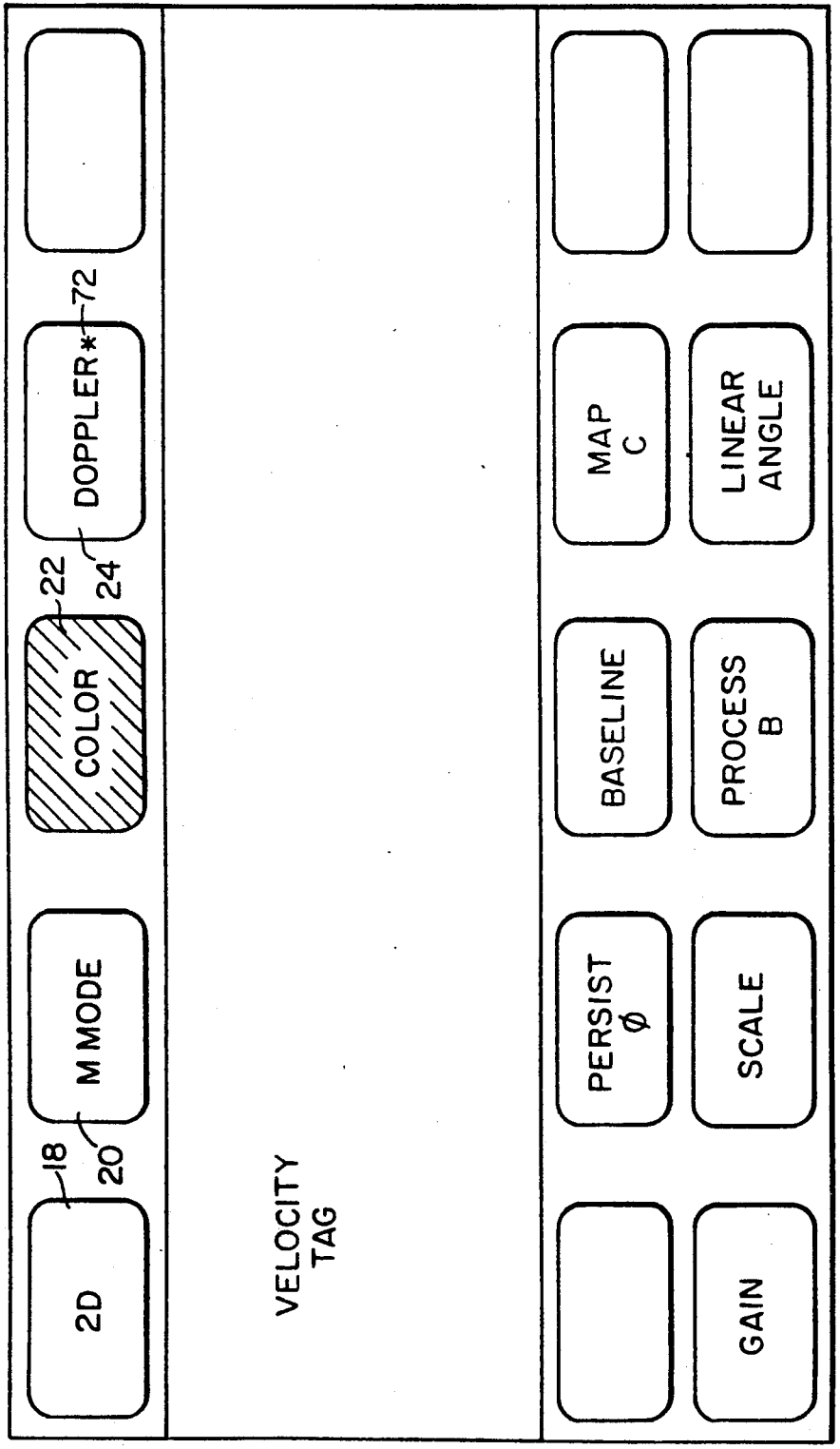

By selecting the COLOR* menu item 22 the user causes the EL panel to change as shown in FIG. 7(e) to display the color flow control set of FIG. 4(a). The system remains in the 2D/CF/PWx color flow Doppler mode, i.e., the displayed control set changes from the Doppler control set of FIG. 7(d) to the color flow control set of FIG. 7(e) but the system state does not change. An asterisk 72 is now displayed in the DOPPLER menu item 24 to indicate that the Doppler mode is still active although the color flow control set is currently shown in the EL panel. The Doppler control set may be redisplayed on the EL panel without changing the system state by selecting the DOPPLER* menu item 24.

Figure 8:
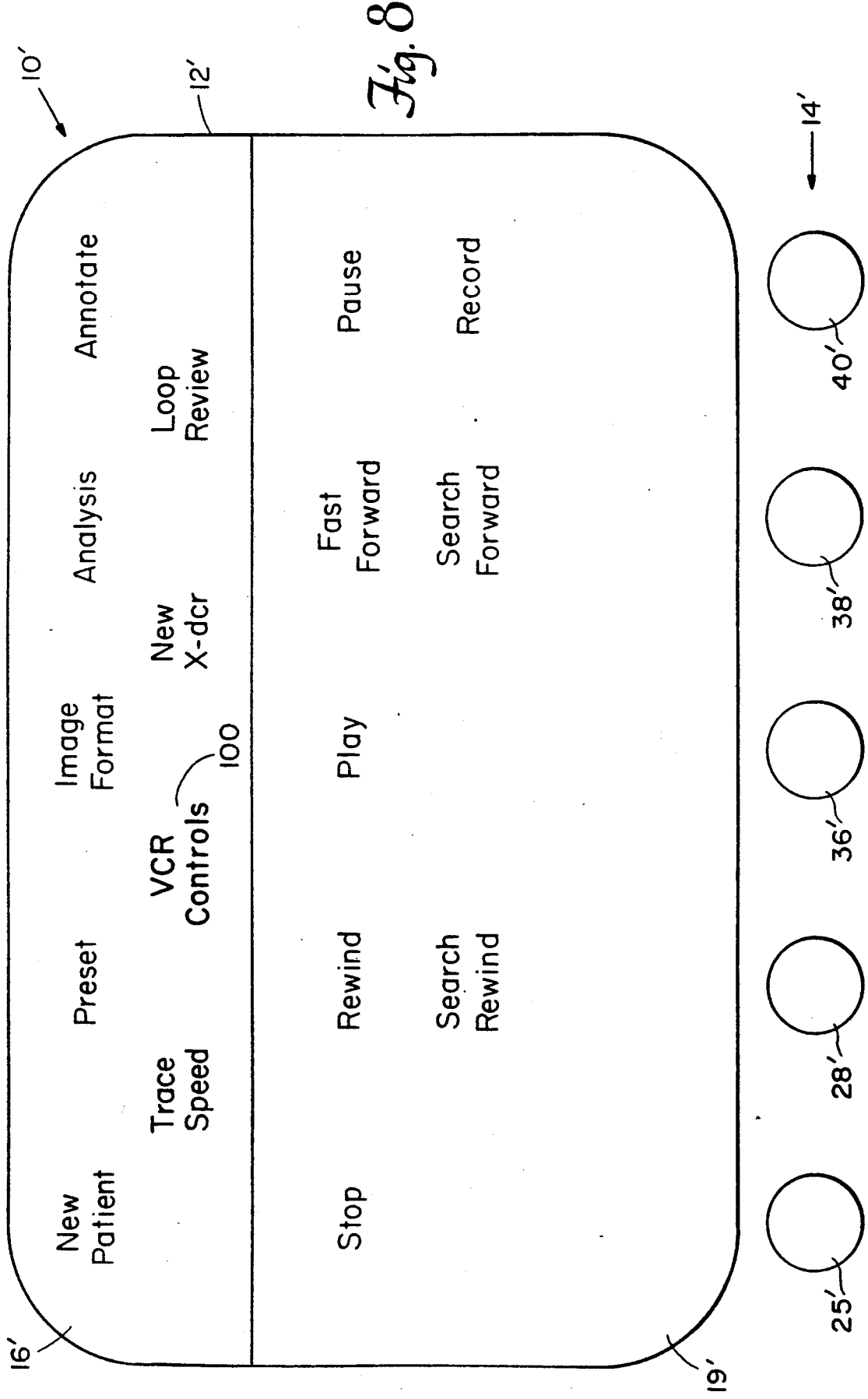
FIG. 8 is a plan view of a second control panel of the invention displaying the non-imaging system control menu.

Referring to FIG. 8, there is shown another example of another EL panel control panel 10' for controlling the non-imaging related functions of a medical ultrasound imaging system. EL panel 12' may be the same EL panel 12 of FIG. 2 with the non-imaging related functions displayed in place of the imaging function, but preferably EL panel 12' is a separate panel mounted adjacent to EL panel 12 so that the user may have imaging and non-imaging controls simultaneously available. It will be appreciated by those skilled in the art that a single EL panel large enough to display both the imaging and non-imaging control sets may be used in place of two separate panels.

The same flat menu hierarchy is employed with the non-imaging controls. The control set selection group 16' displays menu items of available control sets to the user, and functional control group 19' displays menu items available in the selected control set. Here, for instance, the VCR CONTROLS menu item 100 has been selected, and the functional control group 19' displays the familiar VCR control menu items.

Figure 9:
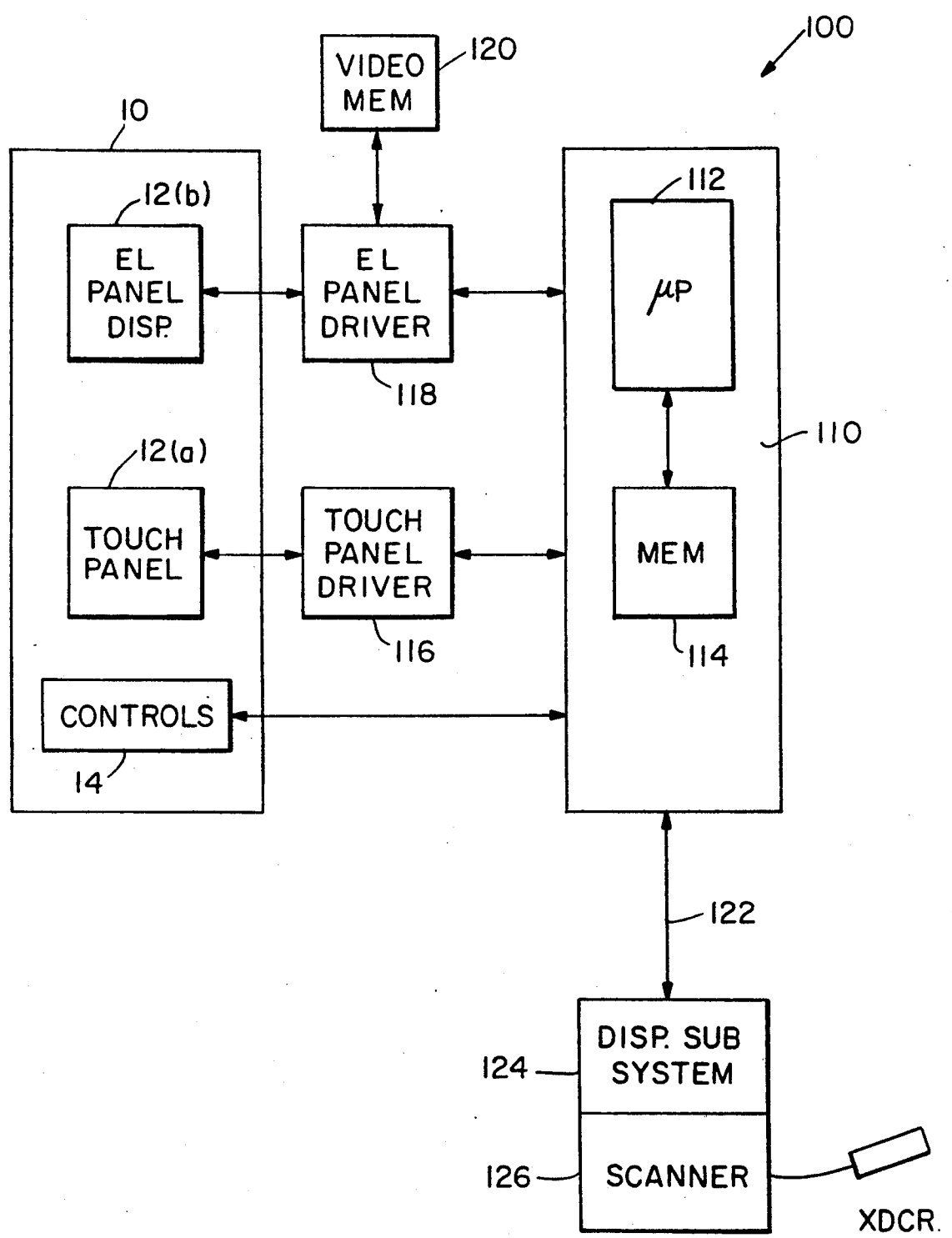
FIG. 9 is a block diagram of a controller for implementing the ultrasound system control panel of FIG. 1.

Referring to FIG. 9, there is shown a block diagram of a controller 100 for implementing the ultrasound system control panel of this invention. Control panel 10 is coupled to a keyboard controller 110 which includes a microprocessor portion 112 that responds to menu handler software instructions stored in a memory 114.

EL touch panel 12 (FIG. 1) is shown as two portions, touch panel 12(a) and EL panel display 12(b). The touch panel 12(a) is connected to the controller 110 through a touch panel driver circuit 116 which allows the controller to communicate with the touch panel, i.e., enable the touch panel to respond to various input and communicate received input to the controller. The EL panel display 12(b) is connected to the controller through an EL panel video driver 118 for displaying menu items on the panel in response to the keyboard controller. A video memory 120 stores the EL panel menu items in video format.

A data communication channel 122 is connected from the keyboard controller 112 to the rest of the ultrasound system including the display subsystem 124 and scanner subsystem 126. The keyboard controller issues commands to the display and scanner subsystems to cause the system to enter various modes in response to user input to the control panel.

While this invention has been particularly shown and described with reference to preferred embodiments thereof, it will be understood by those skilled in the art that various changes in form and details may be made therein without departing from the spirit and scope of the invention as defined by the appended claims.

We claim:

1. An ultrasound imaging system comprising:
    a control panel means comprising a plurality of menu items divided into a first group of menu items and a second group of menu items, said first group of menu items for selecting from a plurality of system modes;
    a display means for displaying said second group of menu items defining a control set of a plurality of system functions corresponding to a selected system mode;
    means for selecting each system mode from the first group of menu items and for providing the second group of menu items to correspond to the selected system mode control set, wherein unselected menu items of the first group of system mode menu items are always available for selection independent of which control set the second group of menu items is displaying.

2. The ultrasound system of claim 1 wherein the display means comprises an electroluminescent panel.

3. The ultrasound system of claim 1 wherein the display means comprises an electroluminescent touch panel, and each menu item function is selectable by touching the corresponding menu item on the display means.

4. The ultrasound system of claim 1 further comprising
    a plurality of control means disposed on the control panel means adjacent to the display means and at least one menu item is displayable for defining the function of at least on of said plurality of control means.

5. The ultrasound system of claim 4 wherein one of said menu items displays the functions available for the control and one of the plurality of functions is selected to define the current function of the control.

6. The ultrasound system of claim 4 wherein the control means comprise at least one rotatable control.

7. The ultrasound system of claim 1 wherein one or more system modes may be activated simultaneously by selecting each desired system mode in sequence from the first group of menu items, each system mode selection causing the sec of menu items to correspond to a previously selected system mode control set.

8. The ultrasound system of claim 1 wherein selecting a menu item from the second group of menu items may display additional system function menu items in the second group.

9. The ultrasound system of claim 1 further comprising
    a second display means for displaying another second group of menu items defining a control set of a plurality of system functions corresponding to the selected system mode.

10. The ultrasound system of claim 9 wherein
    the first display means displays system mode control sets for controlling the imaging aspects; and
    the second display means displays system mode control sets for controlling the non-imaging aspects of the system.

11. A medical ultrasound imaging system comprising:
    a control panel means comprising a plurality of menu items divided into a first group and a second group of menu items, the first group of menu items for selecting from a plurality of system modes,
    a touch panel display means for displaying said second group of menu items defining a control set of a plurality of system functions corresponding to a selected system mode, each menu item being selectable by touching the corresponding menu item;
    a plurality of rotatable controls disposed on the control panel means adjacent to the display means and each rotatable control means corresponding to one or more menu items for defining the function of the rotatable control means;
    means for selecting each system mode from the first group of menu items and for providing the second group of menu items to correspond to the selected system mode control set, wherein the unselected menu items of the first group of system mode menu items are always available for selection independent of which control set the second group of menu items is displaying.

12. The ultrasound system of claim 11 wherein said touch panel display comprises an electroluminescent panel.

13. The ultrasound system of claim 11 wherein said display means displays one of a plurality of menu items with functions available for the rotatable control means and one of the plurality of functions is selectable to define the current function of the rotatable control.

14. The ultrasound system of claim 13 wherein one or more system modes may be activated simultaneously by selecting each desired system mode in sequence from the first group of menu items, each system mode selection causing the second group of menu items to correspond to the last selected system mode control set.

15. The ultrasound system of claim 11 wherein said selectable menu items from the second group of menu items displays additional system function menu items in the second group.

16. The ultrasound system of claim 11 further comprising
    a second display means for displaying another second group of menu items defining a control set of a plurality of system functions corresponding to the selectable system mode.

17. The ultrasound system of claim 16 wherein
    the first display means displays system mode control sets for controlling the imaging aspects of the system; and
    the second display means displays system mode control sets for controlling the non-imaging aspects of the system.

18. A method for controlling an ultrasound system comprising the steps of:
    providing a display of a plurality of menu items;
    displaying a first group of menu items selectable from a plurality of system mode control sets;
    selecting one of the system mode control set menu items from the first group of menu items for the system to enter the selected mode; and
    while displaying the first group of menu items, also displaying a second group of menu items for selecting from a plurality of system functions corresponding to the selected system mode control set.

19. The method of claim 18 further comprising the steps of
   selecting a second system mode control menu item from the first group of menu items for the system to enter the second selected system mode in addition to the previously selected system mode, and
   while displaying the first group of menu items, also displaying the second group of menu items corresponding to the second selected system mode control set.

20. The method of claim 19, further comprising the steps of:
   providing a second display for displaying said second plurality of menu items;
   displaying said first group of menu items, on the second display for selecting from a plurality of system mode control sets;
   selecting one of the system mode control set menu items from the first group of menu items of the second display for the system to enter the selected mode; and
   while displaying the first group of menu items of the second display, also displaying a second group of menu items on the second display for selecting from a plurality of system functions corresponding to the selected system mode control set of the first group of menu items of the second display.

* * * * *